(12) United States Patent
Ferree

(10) Patent No.: US 6,875,235 B2
(45) Date of Patent: Apr. 5, 2005

(54) PROSTHETIC JOINTS WITH CONTAINED COMPRESSIBLE RESILIENT MEMBERS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/435,332

(22) Filed: May 9, 2003

(65) Prior Publication Data

US 2004/0030398 A1 Feb. 12, 2004

Related U.S. Application Data

(63) Continuation-in-part of application No. 10/407,554, filed on Apr. 4, 2003, which is a continuation-in-part of application No. 10/303,385, filed on Nov. 25, 2002, which is a continuation-in-part of application No. 10/191,639, filed on Jul. 9, 2002, which is a continuation-in-part of application No. 09/415,382, filed on Oct. 8, 1999, now Pat. No. 6,419,704
(60) Provisional application No. 60/445,958, filed on Feb. 7, 2003, provisional application No. 60/445,489, filed on Feb. 6, 2003, and provisional application No. 60/379,462, filed on May 10, 2002.

(51) Int. Cl.[7] ................................................. A61F 2/38
(52) U.S. Cl. ............................... 623/20.32; 623/23.41; 623/17.11
(58) Field of Search ......................... 623/20.14–20.38, 623/23.41

(56) References Cited

U.S. PATENT DOCUMENTS

| 3,938,198 | A |   | 2/1976  | Kahn et al. ............... 623/22.15 |
| 4,586,933 | A | * | 5/1986  | Shoji et al. ............... 623/20.29 |
| 4,892,551 | A |   | 1/1990  | Haber ...................... 623/23.17 |
| 4,911,718 | A |   | 3/1990  | Lee et al. ................. 623/17.15 |
| 5,071,437 | A |   | 12/1991 | Steffee .................... 623/17.16 |
| 5,080,675 | A | * | 1/1992  | Lawes et al. ............. 623/20.33 |
| 5,201,881 | A |   | 4/1993  | Evans ...................... 623/20.28 |
| 5,389,107 | A |   | 2/1995  | Nassar et al. ............ 623/23.17 |
| 5,458,643 | A | * | 10/1995 | Oka et al. ................. 623/17.16 |
| 5,534,028 | A |   | 7/1996  | Bao et al. ................. 623/17.16 |
| 5,593,445 | A |   | 1/1997  | Waits ....................... 623/23.42 |
| 5,735,905 | A |   | 4/1998  | Parr ......................... 623/23.11 |
| 5,879,387 | A |   | 3/1999  | Jones et al. .............. 623/18.11 |
| 5,954,722 | A |   | 9/1999  | Bono ........................ 606/61 |
| 5,957,979 | A |   | 9/1999  | Beckman et al. ........ 623/20.33 |
| 5,976,186 | A |   | 11/1999 | Bao et al. ................. 623/17.16 |
| 6,030,389 | A |   | 2/2000  | Wagner et al. ........... 623/17.16 |
| 6,197,065 | B1 |  | 3/2001  | Martin et al. ............ 623/23.17 |
| 6,258,126 | B1 | * | 7/2001  | Colleran .................. 623/20.29 |
| 6,280,475 | B1 |  | 8/2001  | Bao et al. ................. 623/17.16 |
| 6,302,916 | B1 |  | 10/2001 | Townley et al. ......... 623/23.58 |
| 6,319,283 | B1 |  | 11/2001 | Insall et al. .............. 623/20.33 |
| 6,379,388 | B1 |  | 4/2002  | Ensign et al. ............ 623/20.34 |
| 6,508,841 | B2 |  | 1/2003  | Martin et al. ............ 623/23.12 |
| 6,527,806 | B2 |  | 3/2003  | Ralph et al. ............. 623/17.16 |
| 6,569,202 | B2 | * | 5/2003  | Whiteside ................ 623/20.32 |
| 6,620,198 | B2 | * | 9/2003  | Burstein et al. ......... 623/20.28 |
| 6,652,587 | B2 | * | 11/2003 | Felt et al. ................. 623/20.16 |

FOREIGN PATENT DOCUMENTS

WO    WO 00/64385    11/2000    ............. A61F/2/44

* cited by examiner

*Primary Examiner*—David H. Willse
*Assistant Examiner*—Suzette J. Gherbi
(74) *Attorney, Agent, or Firm*—Gifford, Krass, Groh, Sprinkle, Anderson & Citkowski, PC

(57) ABSTRACT

In a total knee replacement (TKR), the use of a cushion element provides better wear characteristics than polyethylene ("poly") alone. Since a metal-on-metal, metal-on-ceramic, or ceramic-on-ceramic articulating surface has better wear characteristics than metal on poly, the invention essentially provides cushioning for metal/ceramic-on-metal/ceramic joint replacements. It also allows the use of elastomers for their cushioning properties rather than their surface wear and tensile strength characteristics. The contained compressible elements could also be used as a cushion below polyethylene components, polyethylene over metal components, unicondylar knee replacements, patellar components, and prosthetic components for other parts of the body, including the hip, elbow, shoulder, wrist, and ankle.

7 Claims, 9 Drawing Sheets

-OR-

PROSTHETIC JOINTS WITH CONTAINED COMPRESSIBLE RESILIENT MEMBERS

REFERENCE TO RELATED APPLICATION

This application claims priority from U.S. Provisional Patent Application Ser. Nos. 60/379,462, filed May 10, 2002; 60/445,489, filed Feb. 6, 2003; and 60/445,958, filed Feb. 7, 2003. This application is also a continuation-in-part of U.S. patent application Ser. No. 10/407,554, filed Apr. 4, 2003, which is a continuation-in-part of U.S. patent application Ser. No. 10/303,385, filed Nov. 25, 2002; which is a continuation-in-part of U.S. patent application Ser. Nos. 10/191,639, filed Jul. 9, 2002 and 09/415,382, filed Oct. 8, 1999, now U.S. Pat. No. 6,419,704. The entire content of each application and patent is incorporated herein by reference.

FIELD OF THE INVENTION

This invention relates generally to prosthetic implants and, more particularly, to devices of this type including contained, compressible, resilient members.

BACKGROUND OF THE INVENTION

In prior art total knee replacements (TKRs), polyethylene trays are placed between metal tibial and femoral components. The metal femoral component articulates with the polyethylene tray. The loads across the TKR and movement between the femoral component and poly tray cause surface wear of the poly. The problems associated with poly wear are well known to Orthopaedic surgeons: fracture of the poly tray, thinning of the tray, migration of poly particles throughout the body, and loosening of the prosthetic joint from the body's reaction to the poly particles. U.S. Pat. No. 6,302,916 describes many of these problems.

Metal-on-metal articulations are seen as an improvement over metal on poly articulations. Metal on metal articulations are reported to have 400× less wear than metal on poly surfaces, but their use has so far been limited.

Surgeons who perform arthroplasty of arthritic joints hope to eliminate pain and restore normal function of the replaced joint. Arthroplasty surface technology attempts to replicate cartilage function. Cartilage surfaces have a very low coefficient of friction. Metal-on-metal surfaces and metal-on-poly surfaces also have low coefficients of friction. Cartilage also provides cushioning or dampening of forces across the joint. Metal-on-metal designs do not provide dampening. Metal-on-poly surfaces provide more dampening than metal on metal surfaces, but they do not the cushioning of cartilage.

The choice of materials for prosthetic implants is also limited by surface wear characteristics of the materials. Metals have better surface wear characteristics than polyethylene, but metals do not provide cushioning. The choice of materials is also limited by the tensile strength of the materials. Materials used to form articular surfaces must withstand the large forces exerted on the joint. The materials must withstand shear and tension forces in addition to compression forces. Polyethylene was chosen as the best material to meet the requirement listed above.

SUMMARY OF THE INVENTION

In broad and general terms, this invention encases, encapsulates, contains, or otherwise protects a compressible/resilient member with one or more rigid components associated with an articulating bone. The embodiments are applicable not only to artificial disc replacement (ADR) devices, but also to joint situations including the knee, hip, elbow, shoulder, wrist, and ankle.

The cushion elements in the preferred embodiments include synthetic rubbers, hydrogels, elastomers, and other polymeric materials such as viscoelastic polymers and foam polyurethanes. The invention effectively combines the advantages of such materials (cushioning, shape memory, and expansion after insertion in the case of hydrogels), while providing increased protection, particularly the elimination of shear stresses.

In a total knee replacement (TKR), the use of a cushion element provides better wear characteristics than polyethylene ("poly") alone. Since a metal-on-metal, metal-on-ceramic, or ceramic-on-ceramic articulating surface has better wear characteristics than metal on poly, the invention essentially provides cushioning for metal/ceramic-on-metal/ceramic joint replacements. It also allows the use of elastomers for their cushioning properties rather than their surface wear and tensile strength characteristics.

The contained compressible elements could also be used as a cushion below polyethylene components, polyethylene over metal components, unicondylar knee replacements, patellar components, and prosthetic components for other parts of the body. All of the embodiments of the invention can be enclosed by a membrane to trap wear debris inside the device. The seal can also hold a lubricating fluid, such as vegetable oil or other oils or gels inside the device. In hydrogel embodiments, the seal can be fluid permeable.

DETAILED DESCRIPTION OF THE INVENTION

This invention address and solves such problems arising in the prior art. The embodiments are applicable not only to ADR devices, but also to joint situations including total knee and hip arthroplasty. The approach effectively combines the advantages of hydrogels (cushioning, shape memory, and expansion after insertion) and rubber or other elastomers (cushioning), while eliminating shear stresses on the polymer. When applied to an ADR, the invention also minimizes the risk of extrusion.

Hydrogels are used in the preferred embodiments. U.S. Pat. Nos. 5,047,055 and 5,192,326 both incorporated by reference, list some of the applicable hydrogels. The small size of the desiccated hydrogel facilitates insertion, after which the hydrogel imbibes fluids and expands. Other non-hydrogel compressible and/or resilient materials may alternatively be used, including elastomers, shape-memory polymers, which would increase in height after they are inserted. As another example of many, non-hydrogel polymers such as acrylics may be used which change shape with a change in temperature. Thus, as used herein, the term "hydrogel" should be taken to include other resilient/compressible materials.

According to the invention, the hydrogels are protected from shear stress, thereby extending longevity. In particular, the hydrogel is contained, constrained or enclosed within a cavity or cylinder which may include one or more pistons. The hydrogel provides cushioning, while the metal pistons facilitate articulation either directly or indirectly with bone surfaces. Thus, the invention offers the advantages of metal-on-metal while providing for cushioning. The hydrogels allow for physiologic tension adjustment since they can change size based upon imbibing fluid and the pressure on the hydrogel. Thus, the hydrogel component of the device can change height to balance the forces against the surrounding tissues.

The cylinder and piston would likely be made of metal such as stainless steel, titanium, chrome cobalt, or other biocompatible metal or ceramic alloy. Surfaces to promote bone ingrowth could be used on the covers. The hydrogel embodiments may incorporate channels for the diffusion of fluids in and out of the cylinder. Optional permeable membranes can also be used to prevent extrusion of the hydrogel through the channels. The permeable membrane traps the hydrogel but allows fluids to move freely across the membrane.

Figure 1A:
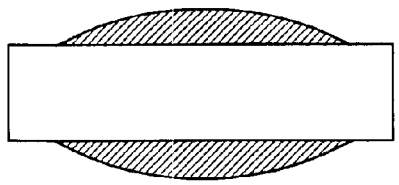
FIG. 1A is a side view of a contained artificial disc replacement (ADR) of the present invention.
Figure 1B:
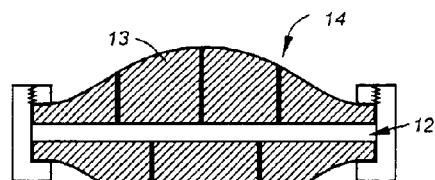
FIG. 1B shows the cross-section of the device of FIG. 1A.
Figure 1C:
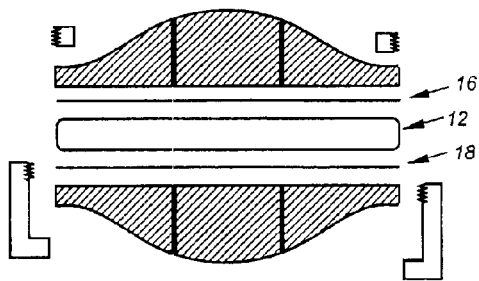
FIG. 1C is an exploded view of the device of FIGS. 1A and 1B.
Figure 1E:
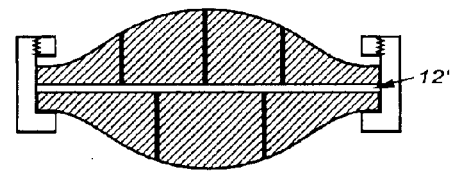
FIG. 1E shows the device in a dehydrated state.
Figure 1D:
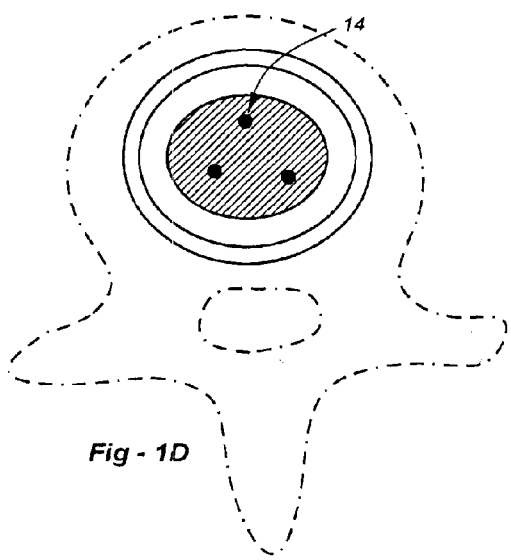
FIG. 1D is a top view of FIGS. 1A–1C in position between a pair of adjacent vertebrae.
Figure 1F:
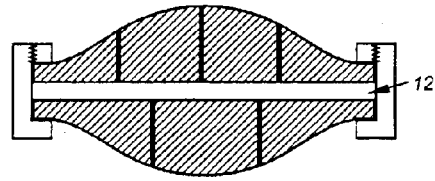
FIG. 1F shows the device in a hydrated/expanded state.

FIG. 1A is a side view of a contained artificial disc replacement (ADR) according to the invention. FIG. 1B is a drawing that shows cross-section of the device of FIG. 1A. Channels through body 13 for fluid migration are shown at 14, and the hydrogel filled chamber is shown at 12. FIG. 1C is an exploded view of the device of FIGS. 1A and 1B. Optional water-permeable membranes are shown at 16 and 18, and the hydrogel layer is shown at 12. FIG. 1D is a top view of FIGS. 1A–1C in position between a pair of adjacent vertebrae. Item 14 shows one of the channels. FIG. 1E shows the device in a dehydrated state, with a narrow space shown at 12'. FIG. 1F shows the device in a hydrated/expanded state with the space 12 expanded after the hydrogel has imbibed fluid.

Figure 2A:
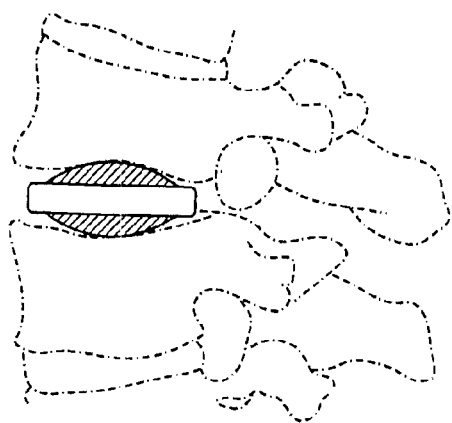
FIG. 2A shows an ADR according to the present invention disposed symmetrically between adjacent vertebrae.
Figure 2B:
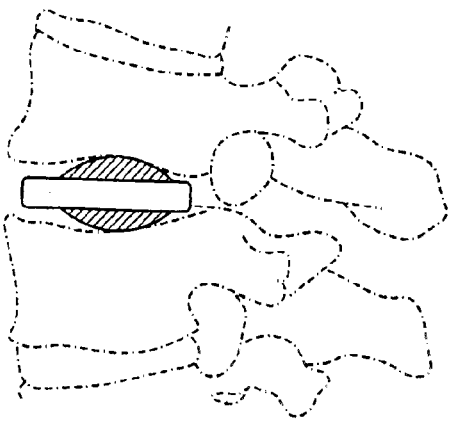
FIG. 2B illustrates an asymmetrical configuration.
Figure 3A:
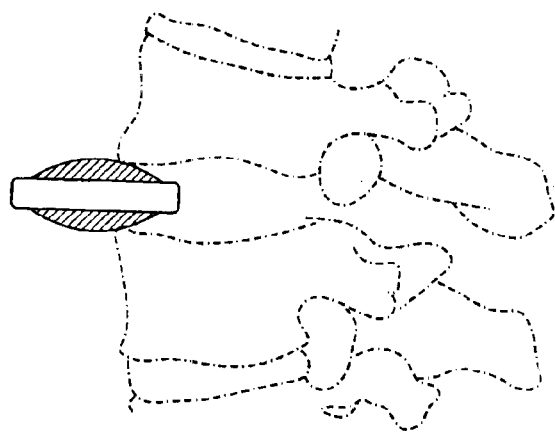
FIG. 3A illustrates a device dehydrated for insertion between the vertebrae.
Figure 3B:
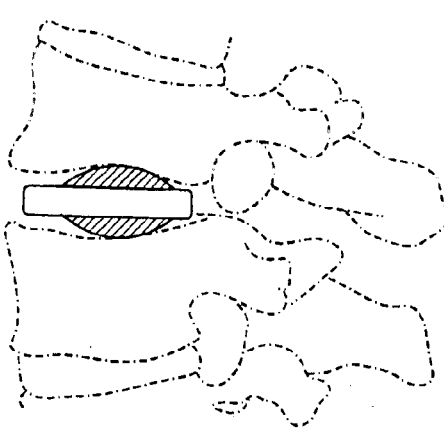
FIG. 3B illustrates the device expanded after insertion and hydration.
Figure 4A:
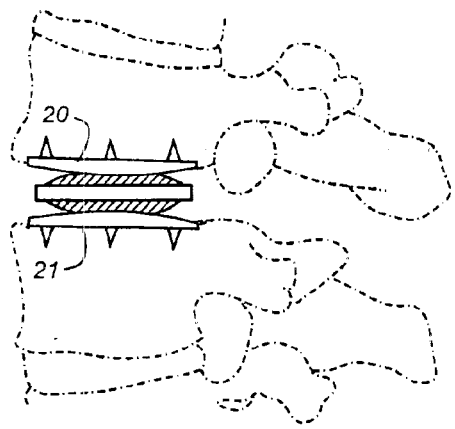
FIG. 4A shows the device of the present invention with endplates in position.
Figure 4B:
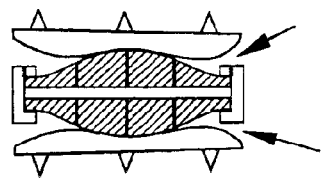
FIG. 4B is a cross-section of FIG. 4A.

Devices according to the invention, regardless of disposition in the body, may be placed symmetrically or asymmetrically. FIG. 2A shows an ADR according to the invention disposed symmetrically between adjacent vertebrae. FIG. 2B illustrates an asymmetrical configuration. FIG. 3A illustrates a device dehydrated for insertion between the vertebrae and FIG. 3B illustrates the device expanded after insertion and hydration. As shown in FIG. 4, endplate covers may be provided in conjunction with the contained hydrogel ADR according to the invention. FIG. 4A shows the device and endplates in position. FIG. 4B is a cross-section with the arrows showing the articulated surfaces.

Figure 5A:
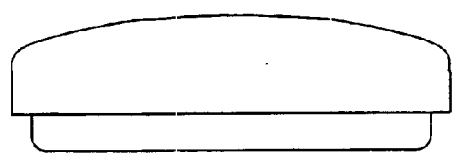
FIG. 5A is a simplified side view of an alternative embodiment of an ADR.
Figure 5B:
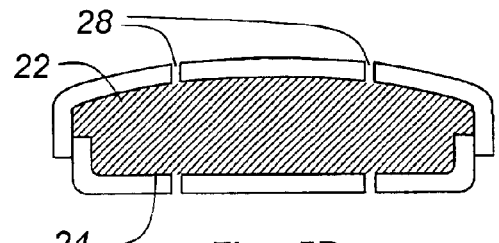
FIG. 5B shows a cross-section of the more encapsulated device showing channels to facilitate fluid transfer.
Figure 5C:
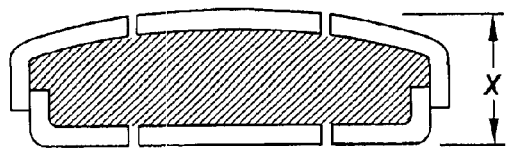
FIG. 5C is a cross-section showing the hydrogel in a desiccated state.
Figure 5D:
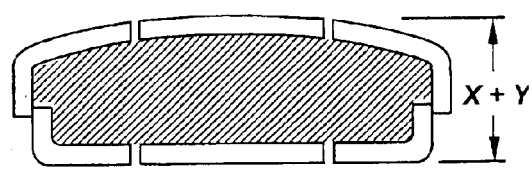
FIG. 5D is a cross-section showing the hydrogel in a hydrated, expanded form.
Figure 5E:
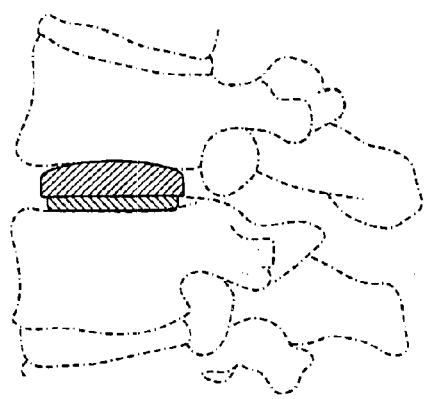
FIG. 5E shows the side view of the device in place between upper and lower vertebrae.
Figure 5F:
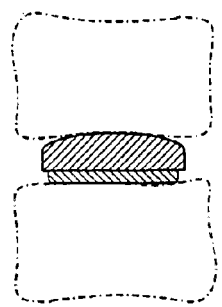
FIG. 5F is an anterior-posterior view of the device in place.
Figure 6A:
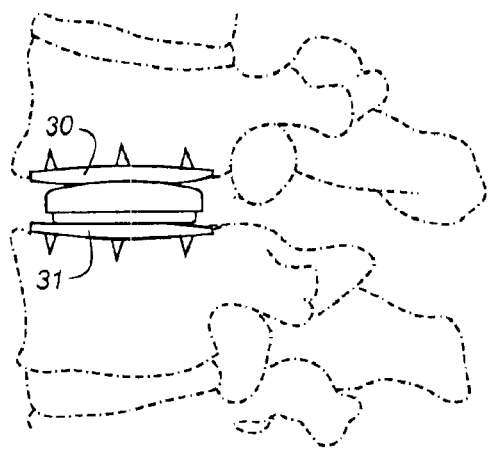
FIG. 6A is a side-view of the device of FIG. 5A with inferior and superior end plates attached to the respective vertebrae.
Figure 6B:
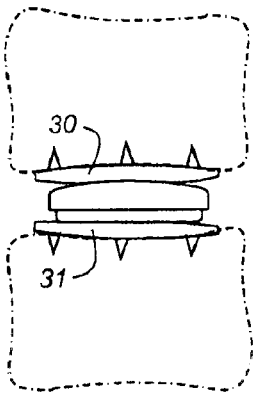
FIG. 6B is an anterior-posterior view of the device of FIG. 6A in position.

FIG. 5A is a simplified side view of an alternative ADR according to the invention, wherein the hydrogel is further encapsulated. FIG. 5B is a cross-section of the more encapsulated device showing channels 28 to facilitate fluid transfer, and a hydrogel 22 and fluid permeable membrane is shown at 24. FIG. 5C is a cross-section showing the hydrogel in a desiccated state having a height "x". FIG. 5D is a cross-section showing the hydrogel in a hydrated, expanded having a height "x+y". FIG. 5E shows the device in place between upper and lower vertebrae from a side view. FIG. 5F is an A–P of the device in place. FIG. 6A is a side-view of the device of FIG. 5, with inferior and superior end plates 30, 31 attached to the respective vertebrae. FIG. 6B is an A–P view of the device of FIG. 6A in position.

Figure 7A:
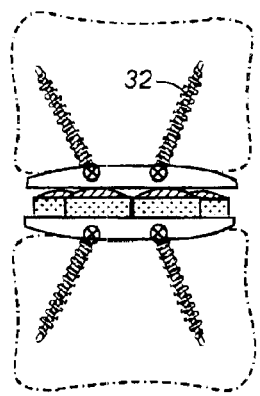
FIG. 7A is an anterior-posterior view of in partial cross-section of an ADR incorporating multiple cylinders.
Figure 7B:
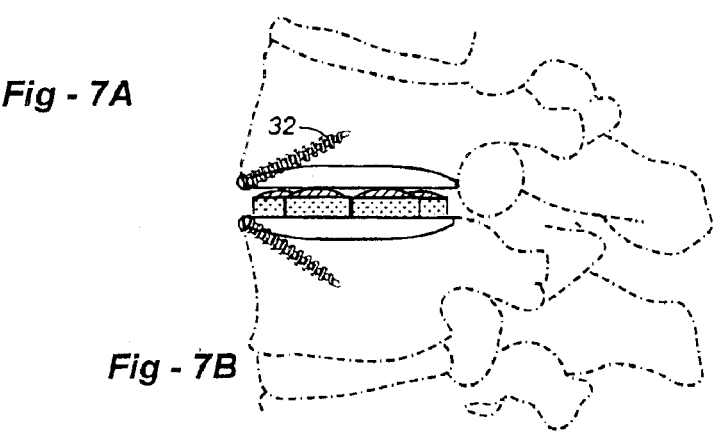
FIG. 7B is a side-view, also in partial cross-section.
Figure 7C:
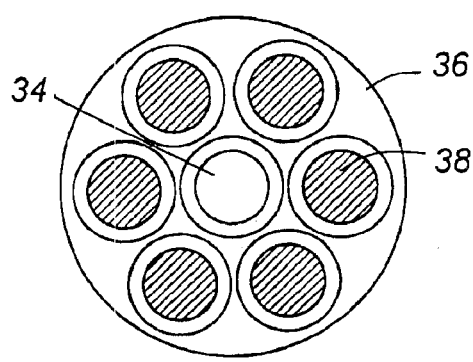
FIG. 7C is an axial cross-section of a device containing a central guide cylinder surrounding six pistons.

The invention may also include two or more cylinders. Adding cylinders reduces the tendency of a single assembly to tilt when pressure is applied in an eccentric fashion. FIG. 7A is an A–P view of in partial cross-section of an ADR incorporating multiple cylinders and end plates attached with screws 32. FIG. 7B is a side-view, also in partial cross-section. FIG. 7C is an axial cross-section of a device containing a metal-ceramic hydrogel cylinder 36, and a central guide cylinder 34 surrounding six pistons 38. It will be appreciated that more or fewer guide cylinders and/or pistons may be used as shown, for example, in FIG. 10.

Figure 7D:
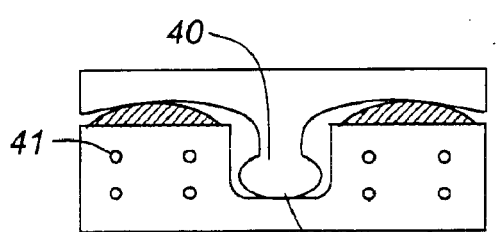
FIG. 7D shows two embodiments with multiple cylinders.
Figure 7D:
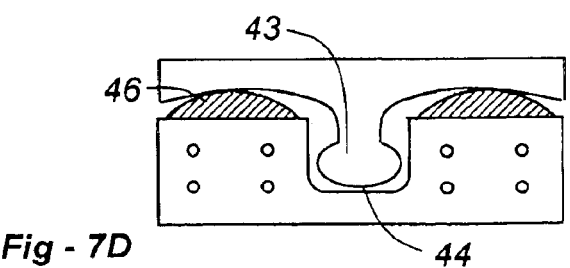

FIG. 7D shows two embodiments with multiple cylinders. In the partial cushion embodiment (upper drawing), the spherical end 42 of the peg 40 projecting from the top plate rests against and is partially supported by a concavity in the lower plate. Holes for fluid transfer are shown at 41. In the full cushion embodiment (lower drawing), the peg projecting from the top plate 43 fits into a restraining cylinder 44. The peg form the top plate does not rest against the bottom plate in this embodiment. A piston is depicted at 46. In either case, the end of the peg is preferably spherical to allow angular motion between the two plates.

Figure 8A:
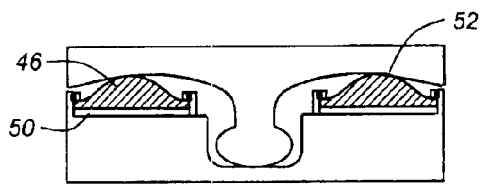
FIG. 8A is a coronal/sagittal cross-section of the cylinders according to the present invention.
Figure 8B:
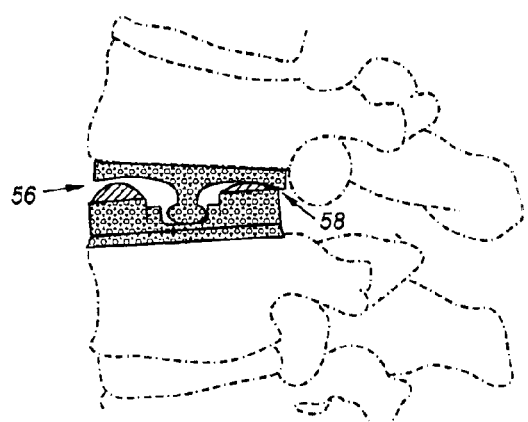
FIG. 8B is an illustration of two vertebrae in extension.
Figure 9:
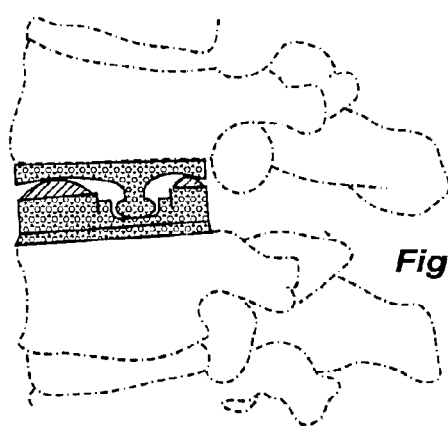
FIG. 9 shows an embodiment with the peg projecting from the posterior aspect of the inferior surface of the upper plate.

FIG. 8A is a coronal/sagittal cross-section of the cylinders according to this embodiment of the invention. A top plate 52 has concavities opposite the piston 46, and the hydrogel layer is shown at 50. FIG. 8B is an illustration of two vertebrae in extension, showing the way in which the front piston is raised 56 and the back piston is lowered 58. Note that the peg that projects from the lower portion of the upper plate need not be central in location. FIG. 9 shows an embodiment with the peg projecting from the posterior aspect of the inferior surface of the upper plate. Posterior peg placement allows a larger anterior cylinder. The larger anterior cylinder may be better at handling the larger forces placed on the anterior portion of the disc replacement during spinal flexion.

Figure 10A:
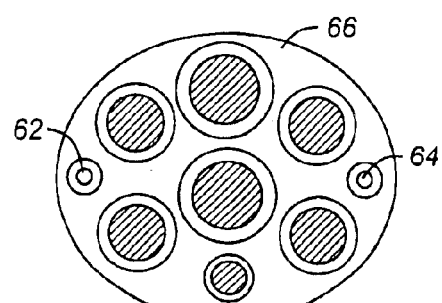
FIG. 10A shows a further alternative embodiment of the present invention.
Figure 10B:
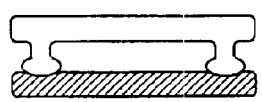
FIG. 10B is a frontal view in cross-section showing partial cushioning.
Figure 10C:
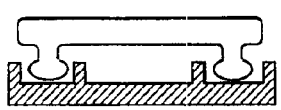
FIG. 10C is a frontal cross-sectional view illustrating full cushioning.
Figure 11B:
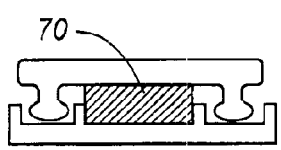
FIG. 11B is a side-view drawing in cross-section showing partial cushioning of the device of FIG. 11A.
Figure 11C:
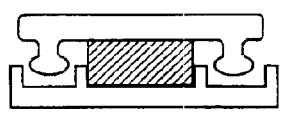
FIG. 11C is a side-view drawing in partial cross-section illustrating the embodiment of FIGS. 11A and 11B.
Figure 11A:
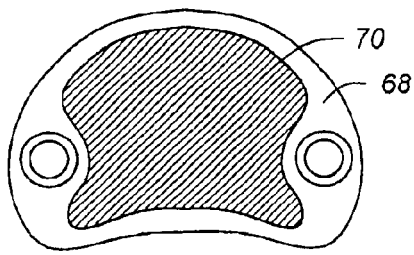
FIG. 11A is a top-down view of an embodiment showing opposing retaining cylinders on either side of a central resilient member.

FIG. 10 is a drawing which shows an alternative arrangement wherein multiple guide cylinders are used at the periphery as opposed to a central location. Among other advantages, this may help to prevent rotatory subluxation of the top component relative to the bottom component while allowing more area centrally for the hydrogels/polymer cylinders. FIG. 10A is a top cross-section view of an embodiment showing multiple peripheral cylinders in housing 66, additional internal hydrogel chambers, and guide cylinders 62, 64. FIG. 10B is a frontal view in cross-section showing partial cushioning. FIG. 10C is a frontal cross-sectional view illustrating full cushioning. Two or more retaining cylinders may also be used to reduce the shear on the solid piece of silicone rubber, elastomer or hydrogel-type material. FIG. 11A is a top-down view of an embodiment 68 showing opposing retaining cylinders on either side of a central resilient member 70. FIG. 11B is a side-view drawing in cross-section showing partial cushioning of the device of FIG. 11A with an elastomer spacer 70. FIG. 11C is a side-view drawing in partial cross-section illustrating the embodiment of FIGS. 11A and 11B providing a full cushioning and reduced shear capability.

Figure 12A:
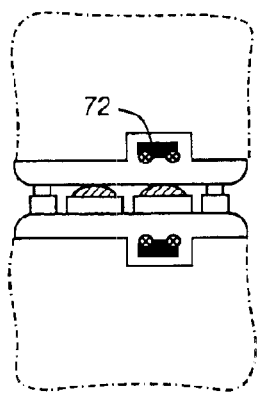
FIG. 12A shows an anterior-posterior view of the embodiment of the invention wherein the end plates of ADR may contain hollow keels on the vertebral side.
Figure 12B:
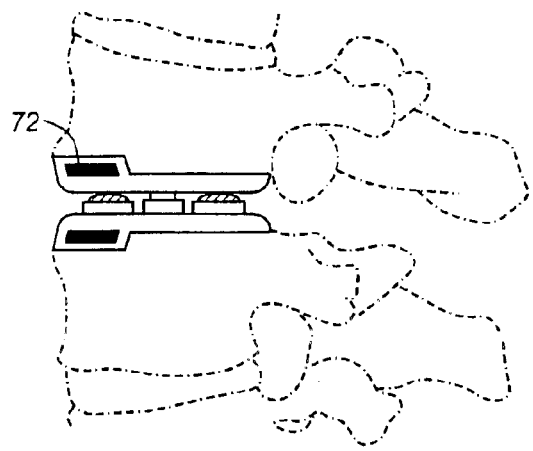
FIG. 12B is a lateral view of FIG. 12A.
Figure 12C:
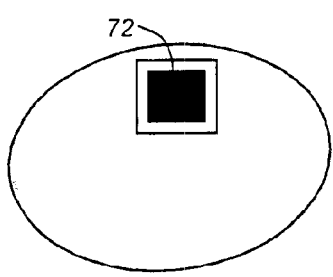
FIG. 12C is a top-down view illustrating the bone ingrowth area of FIG. 12A.

Reference is now made to FIG. 12A, which is an A–P view of the embodiment of the invention wherein the end plates of ADR may contain hollow keels on the vertebral side. FIG. 12B is a lateral view and, FIG. 12C is a top-down view illustrating the bone ingrowth area 72. The vertebrae would be osteotomized to make room for the keels. The bone from the osteomity sites would be morselized and placed inside the hollow keels. The morselized bone would promote ingrowth into the end plates of the ADR, much like hollow cages promote bone ingrowth.

Figure 13:
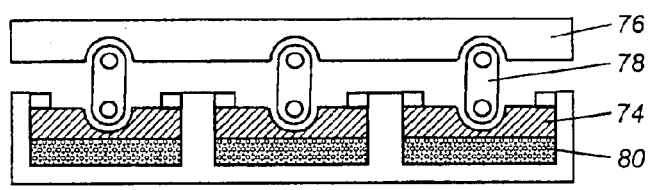
FIG. 13 is a cross-section of an embodiment with multiple pistons connected to the top plate via a rod.
Figure 14A:
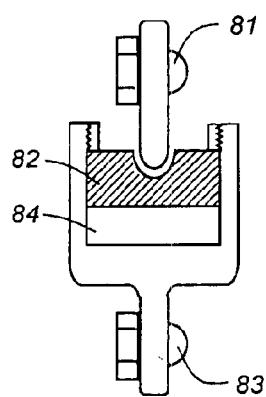
FIG. 14A is a cross-section illustrating an anterior-posterior view of two pedicle scews.
Figure 14B:
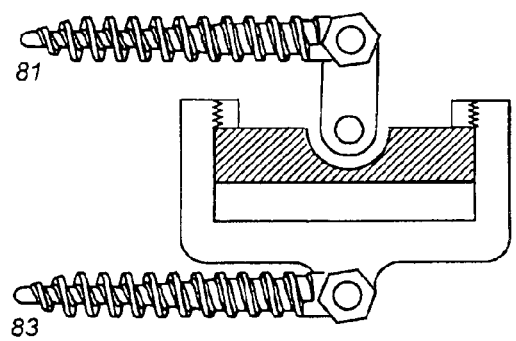
FIG. 14B is a cross-sectional lateral view of the embodiment of FIG. 14A.
Figure 15A:
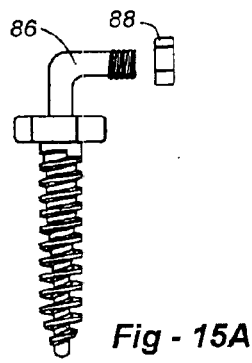
FIG. 15A is a side-view of a pedicle screw having an axle to receive a shock absorber according to the present invention.
Figure 15B:
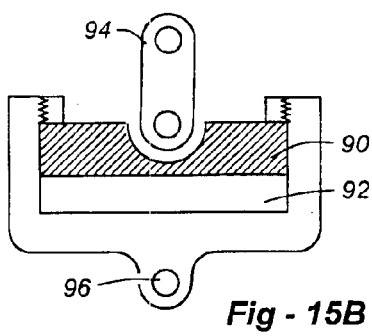
FIG. 15B is a close-up of the shock absorber mechanism associated with a pedicle screw embodiment of FIG. 15A.

FIG. 13 is a cross-section of an embodiment with multiple pistons 74 connected to the top plate via rod 78 that swivels between top endplate 76 and piton 74, much like the design of rods that connect pistons to a crankshaft in an engine. The layer below the pistons is a hydrogel 80. The shock absorber concept according to this invention may also be used with respect to vertebral shock absorbers. FIG. 14A is a cross-section illustrating an A–P view of two pedicle screws 81, 83 coupled in this way. The layer below the pistons 82 is a hydrogel 84. FIG. 14B is a cross-sectional lateral view of the embodiment of FIG. 14A showing screws 81, 83. FIG. 15A is a side-view of a pedicle screw having an axle 86 and nut 88 to receive a shock absorber according to the invention. FIG. 15B is a close-up of the shock absorber mechanism associated with a pedicle screw embodiment. Holes for attachment 94 and 96 are shown with a piston 90 and a hydrogel layer 92.

The cylinders could be made of ceramic, metal, or metal lined with ceramic. The pistons could also be made of metal, ceramic, alloys and so forth. In any case, the articulation of the top and bottom plates is preferably metal-to-metal or ceramic-to-metal, both of which are presumably superior to metal-to-polyethylene articulations. Furthermore, hydrogels, shape memory polymers, or other polymers within the cylinder provide a cushion, or dampen the forces across the plates.

Polymers of different durometers could be used in cylinders in different locations. For example, the polymers in the posterior cylinders could be less compressible and therefore help resist extension of the spine. The cylinders could also use liquids with baffles to dampen motion. That said, hydrogels or polymers have the benefit of functioning without a water tight cylinder piston unit. Indeed, as mentioned previously, the cylinders or the pistons may contain holes to allow fluid movement in the hydrogel configurations.

As discussed above, this invention is not limited to the spine, but may be used in other joint situations such as the knee and hip, which typically use polyethylene bearing surfaces on the acetabulum or proximal tibia. Problems related to polyethylene wear are well known to orthopedic surgeons. Although metal-on-metal and ceramic-on-ceramic total hips have been developed to reduce the problems associated with poly wear, such designs do not provide shock-absorbing capacity. For example, excessive force form tight ligaments about the knee or hip may reduce the size of the hydrogel, thus reducing the tension on the ligaments. Conversely, loose ligaments will cause the hydrogel to swell, thus increasing the tension on the loose ligaments. Although hydrogels are used in this preferred embodiment as well, other elastomers and polymers including shape memory polymers may alternatively be used.

Figure 16:
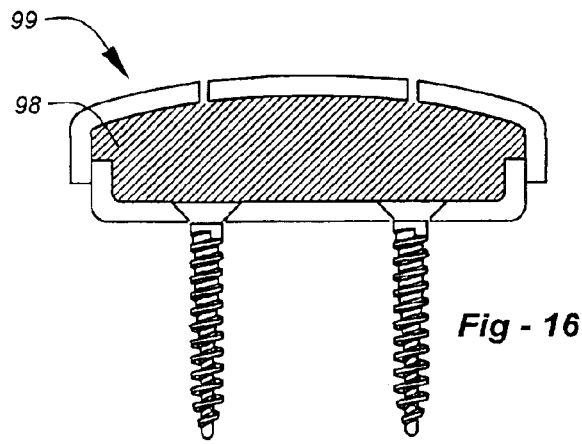
FIG. 16 is a cross-sectional view of a tibial component according to the present invention.
Figure 17:
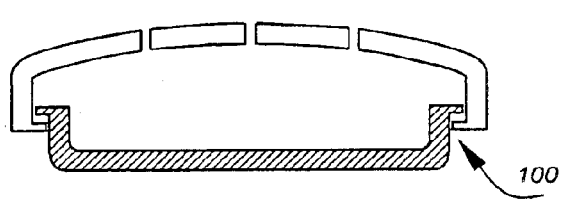
FIG. 17 is a drawing which shows how a locking component may be incorporated in the design.
Figure 18:
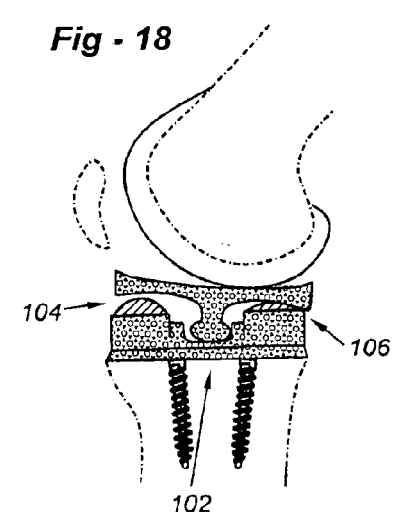
FIG. 18 is a side-view cross-section of a tibial component for a knee replacement.

FIG. 16 is a cross-sectional view of a tibial component according to the invention shown generally at 99. As discussed above, channels are used for fluid transfer, and these may be located around the periphery, or near the center, rather than in the weight-bearing area. Item 98 shows the resilient, fluid-imbibing center. FIG. 17 is a drawing which shows how a locking component 100 may be incorporated in the design which allows movement while, at the same time, prevent disassociation. A similar design may be used for other prosthetic components, including a patella button. FIG. 18 is a side-view cross-section of a tibial component 102 for a knee replacement utilizing a central guide and peripheral pistons, showing the way in which the front piston is raised 104 and the back piston is lowered 106, much like the vertebral embodiments discussed with reference to FIGS. 7–11, in particular.

Figure 19:
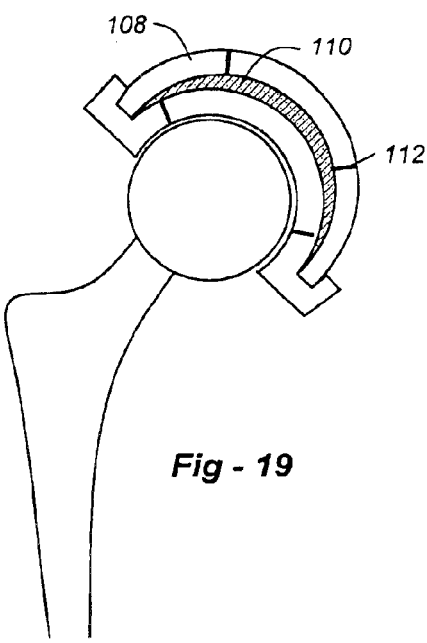
FIG. 19 is a side-view drawing of an embodiment illustrating the way in which the invention may be applied to the hip.

FIG. 19 is a side-view drawing of an embodiment illustrating the way in which the invention may be applied to the hip. As shown in the drawing, an inner cup 108 would be used with respect to the acetabulum, along with an outer bearing surface with a hydrogel/elastomeric or other polymeric material 110 being used therebetween. Particularly with regard to a hydrogel configuration, one or more channels 112 for fluid transfer may be provided.

Figure 20A:
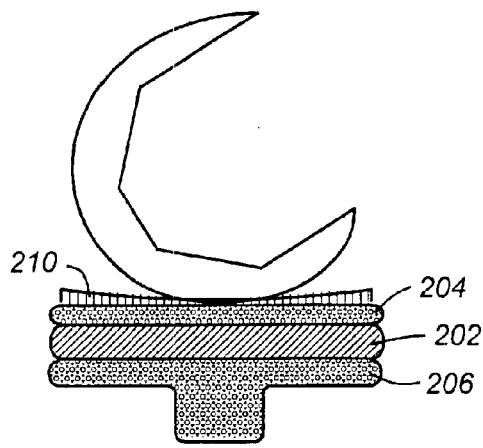
FIG. 20A is a lateral view of an embodiment of the invention applied to total knee replacement.
Figure 20B:
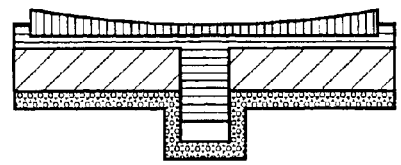
FIG. 20B is sagittal cross section of the embodiment of the device drawn in FIG. 20A.
Figure 20C:
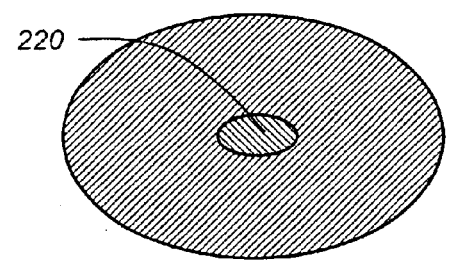
FIG. 20C is a view of the bottom of upper metal component.

FIG. 20A is a lateral view of an embodiment of the invention applied to total knee replacement. A cushion element 202 is located between two metal components 204, 206. The tibial component preferably further includes a polyethylene piece 210. FIG. 20B is sagittal cross section of the embodiment of the device drawn in FIG. 20A. At least one piston configuration is used to limit shear force on the cushion element. FIG. 20C is a view of the bottom of upper metal component. A single piston 220 can be seen on the bottom of the component.

Figure 20D:
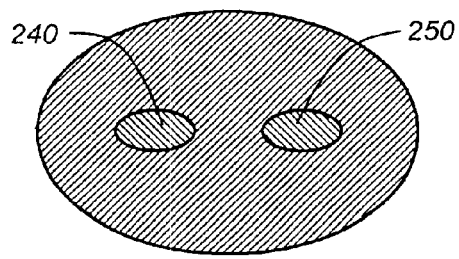
FIG. 20D is a view of the bottom of an alternative embodiment of the component drawn in FIG. 20C incorporating two pistons.
Figure 20E:
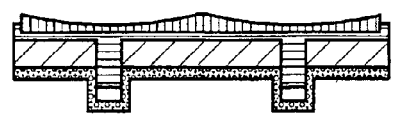
FIG. 20E is a coronal cross section of the embodiment of the device drawn in FIG. 20D.

FIG. 20D is a view of the bottom of an alternative embodiment of the component drawn in FIG. 20C incorporating two pistons 240, 250. Two or more pistons can be used to eliminate rotation between the two metal, or ceramic, components. Eliminating rotation also reduces the shear stresses on the cushion component. FIG. 20E is a coronal cross section of the embodiment of the device drawn in FIG. 20D.

Figure 21A:
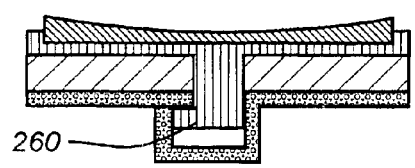
FIG. 21A is a sagittal cross section of an alternative embodiment.
Figure 21B:
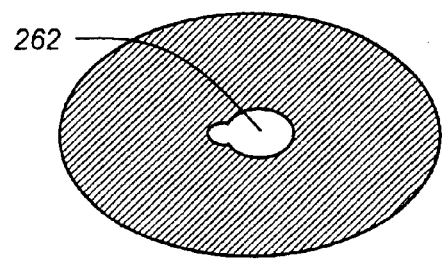
FIG. 21B is a view of the top of the cylinder component of the device drawn in FIG. 21A.

FIG. 21A is a sagittal cross section of an alternative embodiment including an arrangement to lock the components together. A projection 260 from the side of the piston fits into a slot shaped opening 262 in the top of the cylinder. Rotating the two components traps the projection from the piston in the cylinder. FIG. 21B is a view of the top of the cylinder component of the device drawn in FIG. 21A, illustrating the oblong cylinder opening.

Figure 22A:
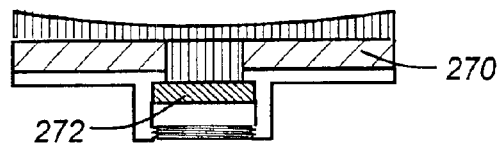
FIG. 22A is a sagittal cross section of an alternative embodiment including a different locking-mechanism.
Figure 22B:
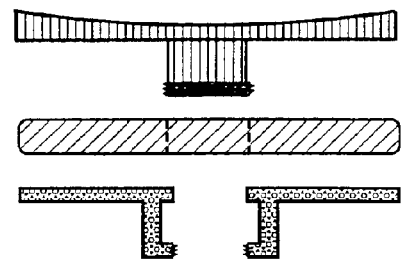
FIG. 22B is an exploded view of the embodiment of the invention drawn in FIG. 22A.

FIG. 22A is a sagittal cross section of an alternative embodiment including a different locking mechanism. The assembled components are locked together. FIG. 22B is an exploded view of the embodiment of the invention drawn in FIG. 22A. The cushion element is illustrated at 270. A preferably circular component 272 is threaded onto the piston, after the piston is placed through cushion component and into the cylinder. A screw 274 is used to close the bottom of the cylinder.

Figure 23:
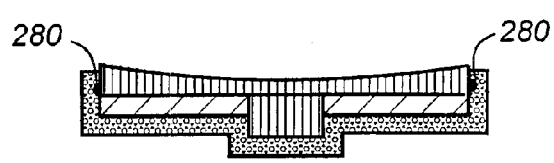
FIG. 23 is a sagittal cross section through a further embodiment of the invention.

FIG. 23 is a sagittal cross section through another embodiment of the invention, wherein a tibia component pistons in the lower component. A seal 280 can be seen between the two components (dark circles). The upper component also has one or more pistons that move within cylinders in the lower component. The upper and lower components can be non-circular in shape to prevent rotation.

Figure 24:
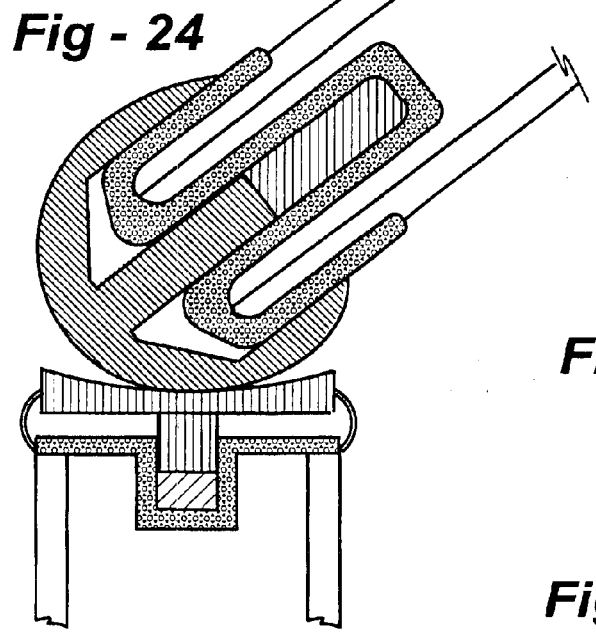
FIG. 24 is a sagittal cross section through yet a further embodiment of the device.

FIG. 24 is a sagittal cross section through another embodiment of the device. The cushion element (area of the drawing with diagonal lines) is contained within cylinders in the tibial and femoral canals. A membrane is used to seal the tibial component. Seals are also illustrated on the femoral components (dark circles).

Figure 25:
FIG. 25 is a sagittal cross section of an alternative embodiment of the invention including hydrogel as a cushion element.
Figure 25:
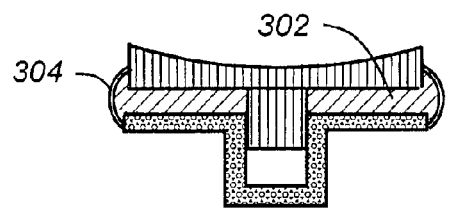

FIG. 25 is a sagittal cross section of an alternative embodiment of the invention including hydrogel as a cushion element 302. A flexible, preferably fluid permeable membrane 304 surrounds the hydrogel. Axial loads on the hydrogel are converted into hoop stress on the flexible membrane. In the preferred embodiment the flexible membrane is elastic. The flexible membrane or components above and below the hydrogel may contain pores for fluid transfer. This embodiment of the device is also described in co-pending U.S. patent application Ser. No. 10/407,554, entitled "Artificial Intervertebral Disc Replacements Incorporating Reinforced Wall Sections."

Figure 26:
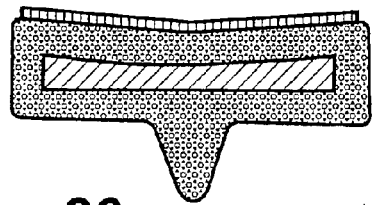
FIG. 26 is a sagittal cross section of an alternative embodiment of the invention wherein the cushion element is enclosed within a flexible metal component.

FIG. 26 is a sagittal cross section of an alternative embodiment of the invention wherein the cushion element is enclosed within a flexible metal component. The cushion component, a sealed elastomer, or hydrogel, for example, is not exposed to the fluids of the body, which can degrade some materials. A somewhat similar device is described in co-pending provisional patent application Ser. No. 60/445, 489, entitled "Improved Longevity Elastic Components For ADRs."

Figure 27:
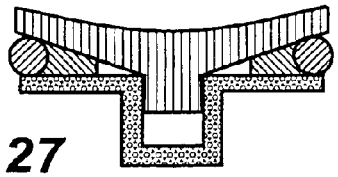
FIG. 27 is a sagittal cross section of another embodiment of the invention.

FIG. 27 is a sagittal cross section of another embodiment of the invention, wherein an elastic component surrounds pieces that move along inclined planes. Loads on the upper tibial component force the moveable outward. The cushion component forces the movable components together as the load is removed from the tibial component. The elastic component is not exposed to shear or compression. The elastic component is only exposed to tension. This embodiment of the device is also described in co-pending provisional patent application Ser. No. 60/445,958, entitled "Composite Components For Disc And Joint Replacements."

I claim:

1. A tibial component configured to articulate with a femoral component associated with a total knee replacement (TKR), comprising:
   a first member configured for fixation to a proximal tibia;
   a second member including a bearing surface oriented toward the femoral component;
   a compressible/resilient member disposed between the first and second members; and
   wherein the first and second members are physically coupled through a piston configuration.

2. The tibial component of claim 1, further including a liner on the bearing surface constructed from polyethylene or other polymer.

3. The tibial component of claim 1, wherein the piston configuration includes a mechanism that allows a certain degree of telescoping while limiting a full pull-out.

4. The tibial component of claim 1, wherein the first and second members are physically coupled through a plurality of pistons.

5. The tibial component of claim 1, wherein the compressible/resilient member is a hydrogel.

6. The tibial component of claim 5, further including a fluid-permeable seal containing the hydrogel.

7. The tibial component of claim 1, further including a fluid-impermeable seal containing the compressible/resilient member.

* * * * *